United States Patent
Chandrapati et al.

(10) Patent No.: US 9,376,703 B2
(45) Date of Patent: Jun. 28, 2016

(54) METHODS FOR DETECTING A XEROPHILIC OR OSMOPHILIC YEAST OR MOLD MICROORGANISM

(71) Applicant: 3M INNOVATIVE PROPERTIES COMPANY, St. Paul, MN (US)

(72) Inventors: Sailaja Chandrapati, Woodbury, MN (US); Tera M. Nordby, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 14/406,538

(22) PCT Filed: May 29, 2013

(86) PCT No.: PCT/US2013/042996
§ 371 (c)(1),
(2) Date: Dec. 9, 2014

(87) PCT Pub. No.: WO2013/188102
PCT Pub. Date: Dec. 19, 2013

(65) Prior Publication Data
US 2015/0132784 A1  May 14, 2015

Related U.S. Application Data

(60) Provisional application No. 61/659,489, filed on Jun. 14, 2012.

(51) Int. Cl.
*C12Q 1/04* (2006.01)
*C12Q 1/44* (2006.01)

(52) U.S. Cl.
CPC .. *C12Q 1/04* (2013.01); *C12Q 1/44* (2013.01); *G01N 2333/37* (2013.01); *G01N 2333/39* (2013.01)

(58) Field of Classification Search
None
See application file for complete search history.

(56) References Cited

U.S. PATENT DOCUMENTS

| 3,881,993 | A | | 5/1975 | Freak et al. | |
|---|---|---|---|---|---|
| 3,968,010 | A | * | 7/1976 | Young | C12Q 1/045 435/287.7 |
| 4,565,783 | A | | 1/1986 | Hansen et al. | |
| 5,089,413 | A | * | 2/1992 | Nelson | C12M 23/04 435/254.1 |
| 5,573,947 | A | | 11/1996 | Madec et al. | |

OTHER PUBLICATIONS

Abdul-Raouf, U.M. et al.; "Comparison of combinations of diluents and media for enumerating *Zygosaccharomyces rouxii* in intermediate water activity foods"; Letters in Applied Microbiology, vol. 19, No. 1, 1994; pp. 28-31.
Atlas, R.; Handbook of Microbiological Media, 3rd Edition; 1993; CRC Press, Boca Raton, FL; pp. Cover, Table of Contents and pp. 2-4 (total 6 pgs.).
Hernandez, P. et al.; "Evaluation of diluents and media for enumerating *Zygosaccharomyces rouxii* in blueberry syrup"; International Journal of Food Microbiology; vol. 25; 1995; pp. 11-18.
ISO 21527-2:2008 "Microbiology of food and animal feeding stuffs—Horizontal method for the enumeration of yeasts and moulds—Part 2: Colony count technique in products with water activity less than or equal to 0,95"; 2008; (15 pgs.).
Andrews, S. et al.; "Optimisation of methodology for enumeration of xerophilic yeasts from foods"; International Journal of Food Microbiology; vol. 35; 1997; pp. 109-116.
Beuchat, L.R. et al.; "Some Considerations When Analyzing Foods for the Presence of Xerophilic Fungi"; Journal of Food Protection; vol. 53, No. 11; 1990; pp. 984-989.

* cited by examiner

*Primary Examiner* — Ralph Gitomer

(57) ABSTRACT

A method for detecting a xerophilic microorganism is provided. The method comprises providing a sample to be tested, an aqueous diluent comprising about 1.0 to about 10.2 weight percent glycerol, and a thin film culture device comprising a cold water-reconstitutable medium to facilitate the growth of a microorganism. The method further comprises mixing the sample with the aqueous diluent to form an inoculum, contacting a predefined amount of the inoculum with the reconstitutable medium to form an inoculated thin film culture device, incubating the inoculated thin film culture device for a period of time, and detecting a presence or an absence of colony of a microorganism. Kits for detecting a xerophilic microorganism according to the method are also provided.

20 Claims, No Drawings

METHODS FOR DETECTING A XEROPHILIC OR OSMOPHILIC YEAST OR MOLD MICROORGANISM

CROSS REFERENCE TO RELATED APPLICATIONS

This application is a national stage filing under 35 U.S.C. 371 of PCT/US2013/042996, filed May 29, 2013, which claims priority to U.S. Provisional Patent Application No. 61/659,489, filed Jun. 14, 2012, the disclosure of which is incorporated by reference in its entirety herein.

BACKGROUND

Indicator testing in the food industry encompasses the microbiological testing of foods for the presence of quality indicator organisms such as total heterotrophic bacteria, coliforms, E. coli, environmental microorganisms belonging to the genus Listeria, yeast, and molds. In spite of recent trends to improve time to result for the detection of these indicator organisms, growth-based yeast and mold tests continue to have the longest incubation time (e.g., 5-7 days) before a result is obtained. As a result, food processors frequently have to wait up to a week before valuable product can be shipped. This results in an inefficient inventory management system.

Certain yeasts and molds require a full 7 days incubation to form observable colonies on the current conventional microbiological media. Among those are yeasts and molds commonly found in low moisture/low water activity (Aw) foods. These microorganisms are commonly characterized as osmophilic yeast and xerophilic molds. Some of the osmophilic and xerophilic microorganisms require the use of sample-suspending media (e.g., aqueous diluents) that contain dissolved solutes (e.g., carbohydrates) at concentrations that protect the microorganisms from osmotic shock when preparing the sample for growth-based testing on microbiological media. The solutes commonly used are sucrose, glucose or glycerol. For example, Abdul-Raouf et al. report the use of diluents comprising 40% or 50% (w/w) glucose or 18% or 26% (w/w) glycerol in an article entitled "Comparison of combinations of diluents and media for enumerating Zygosaccharomyces rouxii in intermediate water activity foods" (Letters in Applied Microbiology, 1994, 19:28-31), which is incorporated herein by reference in its entirety.

In addition, the semi-solid microbiological growth media used to culture xerophilic microorganisms typically comprise at least 18% (w/w) glycerol, at least about 30% (w/w) glucose or at least 20% (w/w) sucrose in order to provide the proper osmotic environment to facilitate growth of these fastidious organisms. Petri dishes containing some of these media must be conditioned in diffuse daylight before use, thereby adding additional time and steps to the testing process.

There remains a need for simpler, faster methods to detect yeast and mold microorganisms in a sample.

SUMMARY

In general, the invention is directed to the detection of a microorganism in a sample. In particular, the present disclosure provides a new sample diluent in a new method of using a thin film culture device to detect yeast or mold microorganisms. The method can be used to detect osmophilic yeast or xerophilic mold microorganisms. Advantageously, the method can be used with a commercially-available thin film culture device to detect and, optionally, quantify yeast and mold microorganisms that include osmophilic yeast and xerophilic molds. The method obviates the need to prepare a growth medium having a low water activity in order to grow and detect osmophilic or xerophilic fungi.

In one aspect, the present disclosure provides a method of detecting yeast or mold microorganisms in a sample. The method can comprise mixing a sample with an aqueous diluent to form an inoculum, contacting a predefined amount of the inoculum with a growth region of a thin film culture device, incubating the inoculated thin film culture device for a period of time, and detecting a presence or an absence of colony of a microorganism in the growth region. The aqueous diluent can comprise about 1.0 to about 10.2 weight percent glycerol. The device can comprise a waterproof substrate having a top surface and a bottom surface; and a dry, cold water-reconstitutable medium fixed to and covering at least a portion of the top surface of the substrate. The medium can comprise guar gum and/or xanthan gum and, optionally, a mixture of nutrients to support the growth of a microorganism. In any of the embodiments, contacting the medium with the predefined amount of the inoculum further can comprise contacting a predefined area of the medium with the predefined amount of the inoculum.

In another aspect, the present disclosure provides a method of detecting a yeast or mold microorganism in a sample. The method can comprise hydrating a growth region of a thin film culture device with a predefined amount of an aqueous diluent, incubating the inoculated thin film culture device for a period of time, and detecting a presence or an absence of colony of a microorganism in the growth region. The aqueous diluent can comprise 1.0 to about 10.2 weight percent glycerol. The thin film culture device can comprise a waterproof substrate having a top surface and a bottom surface; and a dry, cold water-reconstitutable medium fixed to and covering at least a portion of the top surface of the substrate. The medium can comprise guar gum and/or xanthan gum and, optionally, a mixture of nutrients to support the growth of a microorganism.

In any of the above embodiments of the methods, the cover sheet can comprise a first surface and a second surface, wherein the first surface comprises a dry gelling agent adhered thereto, wherein placing the cover sheet over the reconstituted medium comprises contacting a portion of the first surface of the cover sheet with the reconstituted medium. In any of the above embodiments, the device further can comprise an air-permeable membrane having an upper surface and a lower surface, wherein the lower surface of the membrane is fixed to and covering at least a portion of the top surface of the substrate, wherein the reconstitutable medium is fixed to and covering at least a portion of the upper surface of the membrane so as to define a growth region. In any of the above embodiments, the method further can comprise providing a detection reagent, wherein forming a reconstituted medium comprises forming a reconstituted medium comprising the detection reagent. In any of the above embodiments, detecting a presence or an absence of colony of a microorganism can comprise detecting the presence or the absence of an osmophilic microorganism or a xerophilic microorganism. In any of the above embodiments, detecting a presence or an absence of colony of a microorganism can comprise detecting the presence or the absence of a yeast or mold microorganism. In any of the above embodiments, the aqueous diluent can comprise an effective concentration of peptone.

In yet another aspect, the present disclosure provides a kit for detecting a microorganism. The kit can comprise an aqueous diluent comprising about 1.0 to about 10.2 weight percent glycerol. In any embodiment, the kit further can comprise a peptone composition.

In yet another aspect, the present disclosure provides a kit for detecting a microorganism. The kit can comprise an aqueous diluent consisting essentially of about 1.0 to about 10.2 weight percent glycerol. In any embodiment, the kit further can comprise a peptone composition.

In another aspect, the present disclosure provides a kit for detecting a microorganism. The kit can comprise an aqueous diluent consisting essentially of an effective concentration of a peptone and about 1.0 to about 10.2 weight percent glycerol.

In any of the above embodiments, the kit further can comprise a thin film culture device. The device can comprise a waterproof substrate having a top surface and a bottom surface; and a dry, cold water-reconstitutable medium fixed to and covering at least a portion of the top surface of the substrate. The medium can comprise guar gum and/or xanthan gum and, optionally, a mixture of nutrients to support the growth of a microorganism. In any of the above embodiments, the kit further can comprise a reagent for detecting a microorganism.

As used in the instant specification and claims, "air-permeable" designates a membrane that, when substantially exposed at its edge(s) to air, is sufficiently permeable to air in the horizontal direction (i.e., parallel to its surfaces) to provide an adequate supply of air to the overlying medium in order to support the growth of aerobic microorganisms in the medium;

"cold-water-reconstitutable" designates material that is suspendible in water, e.g., forms a dispersion, solution or gel in room temperature water;

"cold-water-soluble" designates a cold-water reconstitutable material that forms a solution or gel in room temperature water;

"growth region" designates the region of each component of a device in which microorganisms are intended to he grown; and "powder" designates a particulate material, e.g., of nutrient and/or gelling agent, wherein the particles have an average diameter suitable for use in a device of the invention, e.g., an average diameter of less than about 400 μm.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to growth-based methods used for the detection of yeast and mold microorganisms in a sample. In particular, the present disclosure provides a method to detect osmophilic or xerophilic microorganisms (e.g., yeast, filamentous fungi) in a sample. "Osmophilic", as used herein, refers to microorganisms that live (e.g., tolerate) or thrive (e.g., grow) in environments having a high osmotic pressure. Osmophilic fungi frequently are designated "xerophilic", which indicates they can grow in a low water activity ($a_w$) environment. Current industry standards prescribe the use of at least two different types of culture medium to detect all of the yeast and mold present in low-moisture foods—one type of medium (e.g., Dichloran Rose Bengal Chloramphenicol (DRBC) agar, Potato Dextrose agar, Acidified Potato Dextrose agar, Sabouraud agar, Glucose Yeast Extract Chloramphenicol agar) to detect non-xerophilic microorganisms and another type of medium (e.g., Dichloran Glycerol (DG18) agar, Malt Salt agar, Glucose Yeast Extract Sucrose agar) to detect xerophilic microorganisms. In addition, current practice recommends the use of high-osmotic strength diluents in the methods of detecting xerophilic microorganisms because the osmotic shock resulting from exposure to low-osmotic strength diluents may reduce the recovery of certain xerophilic microorganisms (P. Hernandez and L. Beuchat. 1995. Intl. J. of Food Microbiol. 25:11-18).

The method of the present disclosure uses a thin film culture device to detect the osmophilic yeast and xerophilic mold. Optionally, the method further comprises quantifying a number of colony-forming units of osmophilic and/or xerophilic microorganisms in the sample. Advantageously, the inventive method permits an operator to detect the growth of the non-osmophilic and/or non-xerophilic microorganisms without the need for a separate culture medium according to conventional methods. In addition, the method further obviates the need for highly-viscous diluents that are difficult to transfer using conventional pipetting techniques.

Osmophilic microorganisms include some very slow-growing yeast belonging to the genus *Zygosaccharomyces*, for example. Nonlimiting examples of osmophilic yeast include *Z bailii* and *Z rouxii*, which are routinely isolated from high sugar-content foods such as honey, jams, jellies, and the like. Xerophilic microorganisms also include filamentous fungi belonging to the genus *Fusarium*, for example. A nonlimiting example of a xerophilic filamentous fungus includes the mold *Fusarium solani*, which is often found in wheat grains and cereals. In addition to their relatively slow growth rates, xerophilic yeast and molds require the use of special diluents in order to preserve osmotic stability during the sample preparation and growth processes.

The method of the present disclosure comprises using a sample to be tested, an aqueous diluent comprising about 1.0 to about 10.2 weight percent glycerol, and a thin film culture device comprising a cold water-reconstitutable medium to facilitate the growth of a microorganism. The method further includes mixing the sample with the aqueous diluent to form an inoculum, contacting a predefined amount of the inoculum with a growth region of the thin film culture device, incubating the inoculated thin film culture device for a period of time, and detecting a presence or an absence of colony of a microorganism in the growth region.

The sample to be tested can be any sample that may comprise a yeast or mold microorganism including, for example, an osmophilic yeast or xerophilic mold microorganism. Nonlimiting examples of suitable samples include environmental samples (e.g., surface swabs) beverages, and food samples (e.g., raw materials, in-process samples, and finished-product samples).

Samples to be tested may include liquids as well as solid(s) dissolved or suspended in a liquid medium. Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. In any embodiment, the sample material may be eluted (e.g., rinsed, scraped, expressed) from the sample-collection device before using the sample material in the method. In some embodiments, liquid or solid samples may be diluted in a liquid (e.g., water, buffer, broth).

Aqueous diluents of the present disclosure comprise a carbohydrate solute to provide osmotic strength to the solution during the process of diluting the sample and to provide additional osmotic strength to the reconstituted medium in the thin film culture device. Suitable carbohydrates include, for example, glycerol. The carbohydrate may be present in the aqueous diluent at a concentration from about 1.0 weight percent to about 10.2 weight percent, inclusive, for example. In a preferred embodiment of the method, the aqueous diluent comprises about 1.0 weight percent to 5.1 weight percent glycerol. In a more preferred embodiment of the method, the aqueous diluent comprises about 2.0 weight percent to 5.1 weight percent glycerol.

Optionally, the aqueous diluent further may comprise an effective concentration of one or more nutrient to facilitate the recovery and/or growth of a microorganism. A preferred nutrient is a peptone. Effective concentrations and types of peptones for facilitating the recovery and/or growth of a microorganism are known in the art (see, for example, pages 2-4 in Ronald Atlas; Handbook of Microbiological Media, $3^{rd}$ Edition; 2004; CRC Press; Boca Raton, Fla.). In a preferred embodiment, the aqueous diluent comprises 0.1 weight percent bacteriological peptone. When sufficient nutrients are provided in the aqueous diluent, the thin film culture device need not comprise a nutrient. A preferred aqueous diluent comprises about 0.1 weight percent peptone and about 1 weight percent to about 10.2 weight percent glycerol; more preferably, the aqueous diluent comprises about 0.1 weight percent peptone and about 1.0 weight percent to about 5.1 weight percent glycerol; even more preferably, the aqueous diluent comprises about 0.1 weight percent peptone and about 2.0 weight percent to about 5.1 weight percent glycerol. A particularly preferred embodiment of the method, the aqueous diluent comprises about 0.1 weight percent peptone and about 5.1 weight percent glycerol.

Optionally, the aqueous diluent further may comprise a detection reagent and/or a buffering agent. Non-limiting examples of suitable detection reagents include dyes (e.g., a pH indicator dye, a redox dye), chromogenic enzyme substrates, and fluorogenic enzyme substrates. Nonlimiting examples of buffering agents include, for example, disodium phosphate, dipotassium phosphate, sodium hydrogen phosphate, potassium hydrogen phosphate, sodium acetate, sodium bicarbonate, and a combination of any two or more of the foregoing buffering agents. In some embodiments, the diluent further may comprise sodium chloride.

Thin film culture devices used in the method of the present disclosure include dry culture medium devices such as, for example, the apparatuses disclosed in U.S. Pat. Nos. 4,565,783 and 5,089,413; which are incorporated herein by reference in their entirety. The thin film culture devices comprise a waterproof substrate having a top surface and a bottom surface; a dry, cold water-reconstitutable medium fixed to and covering at least a portion of the top surface of the substrate so as to define a growth region, the medium comprising guar gum, xanthan gum and, optionally, a mixture of nutrients to support the growth of a microorganism; and a cover sheet. Optionally, the thin film culture device further may comprise a cover sheet. The cover sheet may comprise a first surface and a second surface, wherein the first surface comprises a dry gelling agent adhered thereto. The dry gelling agent can comprise guar gum, xanthan gum, locust bean gum, or a mixture of any two or more of the foregoing gums.

Optionally, the thin film culture device may comprise an indicator (e.g., an enzyme substrate such as, for example, the chromogenic enzyme substrate 5-bromo-4-chloro-3-indolyl phosphate). To grow a yeast or mold sample without interference from bacteria, optional bacteriostatic or bacteriocidal agents such as chloramphenicol, chlortetracycline, tartaric acid, or a suitable penicillin can be included in the thin film culture device.

In some embodiments, the device further may comprise an air-permeable membrane as described in U.S. Pat. No. 5,089,413. The membrane can have an upper surface and a lower surface. In the thin film culture device, the lower surface of the membrane can be fixed to and covering at least a portion of the top surface of the substrate and the reconstitutable medium can be fixed to and covering at least a portion of the upper surface of the membrane so as to define a growth region. Such air-permeable membranes can serve to facilitate the growth of aerobic microorganisms. A non-limiting example of a suitable thin film culture device having an air-permeable membrane is the 3M PETRIFILM Yeast & Mold Count Plate available from 3M Company (St. Paul, Minn.).

In one aspect of the method of the present disclosure, the sample is mixed with the aqueous diluent to form an inoculum. The sample may comprise a liquid, a solid, or a mixture of liquids and solids, as discussed above. In some embodiments, the inoculum is formed by distributing materials collected from the surface of a sample-collection device (e.g., a swab or sponge) into the diluent. In some embodiments, a predefined amount (e.g., one milliliter, one gram) of sample is mixed with a predefined volume (e.g., nine milliliters, ninety nine milliliters) of diluent in order to define a dilution factor that may be used to calculate the number of microorganisms per volume or gram of sample. Mixing the sample with the diluent may optionally include processes such as vortexing and/or stomaching the mixture in order to homogenize the mixture.

After forming the inoculum, the method includes the step of contacting a predefined amount of the inoculum with the reconstitutable culture medium to form a reconstituted medium. In an embodiment where the aqueous diluent comprises 0.1% (w/v) peptone, it follows that the reconstituted medium also comprises 0.1% (w/v) peptone. Typically, the predefined volume is about 1 milliliter, although the amount of inoculum can be varied with the size of the growth area used in the thin film culture device (i.e., if a smaller inoculum volume is used, a proportionally smaller growth area should be used in the thin film culture device. Conversely, if a larger inoculum volume is used, a proportionally larger growth area should be used. A liquid-sample transfer device (e.g., a pipette) is typically used to inoculate the culture device. After the sample has been transferred to the culture device, the device is typically covered (e.g., using the cover sheet, as described in U.S. Pat. Nos. 4,565,783 and 5,089,413) to prevent desiccation and/or contamination.

In some embodiments of the thin film culture device, the cover sheet comprises a first surface and a second surface, wherein the first surface comprises a dry gelling agent (e.g., a dry gelling agent comprising guar gum, xanthan gum, locust bean gum, or a mixture of guar gum, locust bean gum, and/or xanthan gum) adhered thereto. In these embodiments, placing the cover sheet over the reconstituted medium can comprise contacting a portion of the first surface of the cover sheet with the reconstituted medium.

In some embodiments, contacting a predefined amount of the inoculum with the reconstitutable culture medium to form a reconstituted medium further comprises contacting a predefined area of the medium with the predefined amount of the inoculum. The predefined area may be defined, for example, by a hole in a spacer, as shown in FIG. 2 of U.S. Pat. No. 5,089,413. Alternatively, the predefined area may be defined, for example, by an accessory device (e.g., a spreader, such as the spreader available from 3M Company to inoculate PETRIFILM thin film culture devices) that is used to inoculate thin film culture devices.

Using an alternative inoculation technique, the method of the present disclosure can be used for surface plating techniques. Surface plating techniques involve applying the sample to the surface of a pre-hydrated thin film culture device. The sample can be applied, for example, by a plate-streaking technique, by a surface contact technique (e.g., similar to Rodac plates), by rolling or streaking a sample acquisition device (e.g., a swab) onto the prehydrated medium, or by transferring a liquid or solid sample to the surface of a pre-hydrated thin film culture device. In this embodiment, the thin film culture device is rehydrated with a predetermined volume (e.g., 1 milliliter) of aqueous diluent that does not comprise sample material. The aqueous diluent comprises about 1.0 to about 10.2 weight percent glycerol. Optionally, the aqueous diluent further comprises peptone (e.g., about 0.1 weight percent peptone). The diluent is spread over the growth area as described herein. The cover film, if present, is closed over the growth area and the cold-water gelling agents are allowed to gel (e.g., at room temperature) for about 5-30 minutes or longer. The culture device is subsequently opened and the sample is applied to the growth area of the prehydrated culture device.

After the thin film culture device is inoculated according to any of the above embodiments, the method includes the step of incubating the inoculated culture device for a period of time. The culture device is incubated at a temperature that is suitable for growth of xerophilic microorganisms. Temperatures suitable for the growth of xerophilic microorganisms are known in the art and include, for example, incubation temperatures ranging from ambient (ca. 25° C.) to about 32° C. In certain preferred embodiments, the inoculated thin film culture devices are incubated at 25° C. or 28 C.

The method further comprises detecting a presence or an absence of colony of a microorganism. Detecting the presence of a colony may comprise visually observing a microorganism colony in the growth area of the culture device. The colony may be observed, for example because it is colored (e.g., by a pigment it produces and/or by metabolizing a chromogenic or fluorogenic enzyme substrate) in a way that contrasts with the reconstituted culture medium. Thus, in some embodiments, detecting the growth of a microorganism can comprise detecting a metabolic product of the detection reagent (e.g., a fluorogenic or chromogenic enzyme substrate).

Additionally, or alternatively, detecting the presence of a colony can comprise using an imaging system to obtain an image of the thin film culture device and observing or analyzing the image. Analyzing the image may comprise using an image processor to analyze the image according to an image analysis protocol. A nonlimiting example of an automated system for colony detection is the 3M PETRIFILM Plate Reader (available from 3M Company, St. Paul, Minn.).

According to the method, detecting the presence of a xerophilic colony comprises detecting the presence of a colony after about 5 days of incubation (e.g., incubation at 25° C.). Some of the xerophilic microorganism colonies may be detectable after about 3 days of incubation.

According to the method of the present disclosure, detecting a presence or an absence of colony of a microorganism further can comprise quantifying the number of xerophilic colony-forming units in the sample. This is done simply by counting the number of colonies in the growth zone and multiplying the number of colonies by the dilution factor to obtain the number of colony-forming units of osmophilic and/or xerophilic microorganisms per gram (or milliliter) of undiluted sample.

The present disclosure also provides a kit for detecting an osmophililc or a xerophilic microorganism. The kit may comprise an aqueous diluent comprising about 1.0 to about 10.2 weight percent glycerol. The diluent can be used, for example in any embodiment of the method for detecting a microorganism as described herein. In an alternative embodiment, the kit may comprise an aqueous diluent consisting essentially of about 1.0 to about 10.2 weight percent glycerol. In any of the above embodiments, the kit further may comprise a peptone composition. In some embodiments, the peptone composition may comprise a dry, powdered peptone composition, optionally provided in predetermined quantities that may be added to the aqueous diluent. In some embodiments, the peptone composition may comprise a solution (e.g., an aqueous solution) comprising peptone. Optionally the peptone solution may be provided as a sterile solution.

The peptone solution comprises a concentration of peptone that, when mixed with the aqueous diluent in a thin film culture device according to the present disclosure, provides a final concentration of peptone in the reconstituted medium that is effective to facilitate the recovery and/or growth of a xerophilic microorganism. An example of an effective concentration of peptone is 0.1 weight percent. Thus, by way of example, a kit according to the present disclosure may comprise a solution containing 10% (w/v) peptone. The exemplary 10% peptone solution can be diluted with the aqueous diluent (1 part peptone solution per 99 parts aqueous diluent), before or after mixing the sample with the aqueous diluent, to obtain an effective amount of the peptone in the final mixture.

In an alternative embodiment, a kit according to the present disclosure may comprise an aqueous diluent consisting essentially of an effective concentration of a peptone, as described above, and about 1.0 to about 10.2 weight percent glycerol.

In any of the above embodiments of a kit according to the present disclosure, the kit further may comprise a thin film culture device for growing microorganisms. The device may comprise a waterproof substrate having a top surface and a bottom surface; a dry, cold water-reconstitutable medium fixed to and covering at least a portion of the top surface of the substrate so as to define a growth region, the medium comprising guar gum, xanthan gum, and, optionally, a mixture of nutrients to support the growth of a microorganism; and a cover sheet.

In any of the above embodiments of the kit, the aqueous diluent can comprise about 1.0 to about 5.1 weight percent glycerol. In any of the above embodiments of the kit, the kit further can comprise a reagent for detecting a microorganism, as described herein. In some embodiments, the detection reagent can be disposed in the aqueous diluent. In any of the above embodiments of the kit, the kit further may include instructions for detecting an osmophilic yeast and/or xerophilic mold microorganism in a sample. The instructions may include a method of detecting an osmophilic or xerophilic microorganism according to any of the embodiments of the method disclosed herein.

Embodiments

Embodiment A is a method of detecting a yeast or mold microorganism in a sample; the method comprising:
mixing a sample with an aqueous diluent to form an inoculum;
wherein the aqueous diluent comprises 1.0 to about 10.2 weight percent glycerol;
contacting a predefined amount of the inoculum with a growth region of a thin film culture device, the device comprising:
a waterproof substrate having a top surface and a bottom surface;
a dry, cold water-reconstitutable medium fixed to and covering at least a portion of the top surface of the substrate, the medium comprising guar gum and/or xanthan gum and, optionally, a mixture of nutrients to support the growth of a microorganism;
incubating the inoculated thin film culture device for a period of time; and
detecting a presence or an absence of colony of a microorganism in the growth region.

Embodiment B is a method of detecting a yeast or mold microorganism in a sample; the method comprising:
hydrating a growth region of a thin film culture device with a predefined amount of an aqueous diluent;
wherein the aqueous diluent comprises 1.0 to about 10.2 weight percent glycerol;
wherein the thin film culture device comprises:
a waterproof substrate having a top surface and a bottom surface;
a dry, cold water-reconstitutable medium fixed to and covering at least a portion of the top surface of the substrate, the medium comprising guar gum and/or xanthan gum and, optionally, a mixture of nutrients to support the growth of a microorganism;
incubating the inoculated thin film culture device for a period of time; and
detecting a presence or an absence of colony of a microorganism in the growth region.

Embodiment C is the method of Embodiment A or Embodiment B, wherein the aqueous diluent comprises about 1.0 to about 5.1 weight percent glycerol.

Embodiment D is the method of Embodiment A or Embodiment C, wherein contacting the medium with the predefined amount of the inoculum further comprises contacting a predefined area of the medium with the predefined amount of the inoculum.

Embodiment E is the method of any one of the preceding Embodiments, wherein the cover sheet comprises a first surface and a second surface, wherein the first surface comprises a dry gelling agent adhered thereto, wherein placing the cover sheet over the reconstituted medium comprises contacting a portion of the first surface of the cover sheet with the reconstituted medium.

Embodiment F is the method of Embodiment E, wherein the dry gelling agent comprises guar gum, xanthan gum, or a mixture of guar gum and xanthan gum.

Embodiment G is the method of any one of the preceding Embodiments, wherein the device further comprises an air-permeable membrane having an upper surface and a lower surface, wherein the lower surface of the membrane is fixed to and covering at least a portion of the top surface of the substrate, wherein the reconstitutable medium is fixed to and covering at least a portion of the upper surface of the membrane so as to define a growth region.

Embodiment H is the method of any one of the preceding Embodiments, wherein the method further comprises providing a detection reagent, wherein forming a reconstituted medium comprises forming a reconstituted medium comprising the detection reagent.

Embodiment I is the method of Embodiment H, wherein detecting the growth of a microorganism comprises detecting a metabolic product of the detection reagent.

Embodiment J is the method of Embodiment H or Embodiment I, wherein the detection reagent comprises an enzyme substrate for a phosphatase enzyme activity.

Embodiment K is the method of any one of the preceding Embodiments, wherein incubating the inoculated thin film culture device comprises incubating the reconstituted medium at 25 degrees C. for 72 to 168 hours.

Embodiment L is the method of any one of Embodiments A through J, wherein incubating the reconstituted medium comprises incubating the inoculated thin film culture device at 28 degrees C. for 72 to 168 hours.

Embodiment M is the method of any one of the preceding Embodiments, wherein detecting a presence or an absence of colony of a microorganism comprises detecting the presence or the absence of an osmophilic microorganism or a xerophilic microorganism.

Embodiment N is the method of embodiment M, wherein detecting a presence or an absence of colony of a microorganism comprises detecting the presence or the absence of a xerophilic microorganism.

Embodiment O is the method of Embodiment M, wherein the yeast colony comprises yeast cells of the genus *Zygosaccharomyces*.

Embodiment P is the method of Embodiment M, wherein detecting a presence or an absence of colony of a microorganism comprising detecting the presence or the absence of a mold colony.

Embodiment Q is the method of Embodiment P, wherein the colony comprises mold cells of the genus *Fusarium*.

Embodiment R is the method of any one of the preceding Embodiments, wherein the aqueous diluent comprises an effective concentration of peptone.

Embodiment S is the method of Embodiment R, wherein the aqueous diluent further comprises a buffering agent.

Embodiment T is a kit for detecting a microorganism, the kit comprising an aqueous diluent comprising about 1.0 to about 10.2 weight percent glycerol.

Embodiment U is the kit for detecting a microorganism, the kit comprising an aqueous diluent consisting essentially of about 1.0 to about 10.2 weight percent glycerol.

Embodiment V is the kit of embodiment T or embodiment U, further comprising a peptone composition.

Embodiment W is a kit for detecting a microorganism, the kit comprising an aqueous diluent consisting essentially of:
an effective concentration of a peptone; and
about 1.0 to about 10.2 weight percent glycerol.

Embodiment X is the kit of any one of Embodiments T-W, further comprising a thin film culture device for growing microorganisms, the device comprising:
a waterproof substrate having a top surface and a bottom surface; and
a dry, cold water-reconstitutable medium fixed to and covering at least a portion of the top surface of the substrate so as to define a growth region, the medium comprising guar gum and/or xanthan gum and, optionally, a mixture of nutrients to support the growth of a microorganism.

Embodiment Y is the kit of any one of Embodiment X, wherein the aqueous diluent comprises about 5.1 weight percent glycerol.

Embodiment Z is the kit of any one of Embodiments T through Y, further comprising a reagent for detecting a microorganism.

Embodiment AA is the kit of embodiment Z, wherein the reagent is disposed in the aqueous diluent.

Objects and advantages of this invention are further illustrated by the following examples, but the particular materials and amounts thereof recited in these examples, as well as other conditions and details, should not be construed to unduly limit this invention.

EXAMPLES

Method for Detecting Osmophilic Yeast 0.1% Peptone water blanks (Catalog # D299) were obtained from Hardy Diagnostics (Santa Maria, Calif.). Glycerol (Catalog # GX0185-6; >95% ACS grade, obtained from EMD, Billerica Mass.) was added to individual peptone water blanks to achieve a final concentration of 0% (v/v), 1% (v/v), 2% (v/v), 5% (v/v) and 10% (v/v). Yeast strains *Zygosaccharomyces bailii* (ATCC MYA-4549) and *Zygosaccharomyces rouxii* (ATCC 28253) were obtained from Microbiologics Inc (St Cloud Minn.). A single lyophilized disc of each strain was separately added into 10 milliliters of warm (37° C.) 0.1% peptone water to resuspend the organisms from the lyophilized disc material. Thin film culture devices (3M PETRIFILM Yeast & Mold Count Plates) were obtained from 3M Company (St. Paul, Minn.).

Duplicate 3M PETRIFILM plates were inoculated with serially diluted samples of the resuspended lyophilized cultures of *Zygosaccharomyces* spp. (*Z. bailii* and *Z. rouxii*, respectively) by lifting the top film and placing the inoculum on the bottom film. The sample was uniformly spread to the desired surface area (30 mm$^2$) using the spreading device provided by the manufacturer (3M). Inoculated plates were incubated at 25° C. for 5 days. Visible colonies (beige or light blue) were indicative of bacterial growth and were enumerated by counting the number of colored colonies present on the plate. The results are shown in Table 1.

TABLE 1

Colony counts. All plates were observed and counted after 5 days of incubation at 25° C.

| | Glycerol Concentration (v %) | | | | |
|---|---|---|---|---|---|
| | 0% | 1% | 2% | 5% | 10% |
| Z bailii | − | ++ | ++ | ++ | ++ |
| Z rouxii | − | + | ++ | ++ | ++ |

−: No visible growth
+: Relatively smaller number of visible colonies.
++ Relatively larger number of visible colonies.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of detecting yeast or mold microorganisms in a sample; the method comprising:
mixing a sample with an aqueous diluent to form an inoculum;
wherein the aqueous diluent comprises about 1.0 to about 10.2 weight percent glycerol;
contacting a predefined amount of the inoculum with a growth region of a thin film culture device, the device comprising:
a waterproof substrate having a top surface and a bottom surface;
a dry, cold water-reconstitutable medium fixed to and covering at least a portion of the top surface of the substrate, the medium comprising a gelling agent and, optionally, a mixture of nutrients to support the growth of a microorganism;

wherein the gelling agent comprises guar gum, xanthan gum, locust bean gum, or a mixture of any two or more of the foregoing gums;

after contacting the predefined amount of the inoculum with the growth region, incubating the thin film culture device for a period of time at a temperature suitable for growth of a yeast or mold microorganism; and detecting a presence or an absence of colony of the yeast or mold microorganism in the growth region.

2. The method of claim 1, wherein the aqueous diluent comprises about 1.0 to about 5.1 weight percent glycerol.

3. The method of claim 1, wherein contacting the medium with the predefined amount of the inoculum further comprises contacting a predefined area of the medium with the predefined amount of the inoculum.

4. The method of claim 1, wherein the device further comprises an air-permeable membrane having an upper surface and a lower surface, wherein the lower surface of the membrane is fixed to and covering at least a portion of the top surface of the substrate, wherein the reconstitutable medium is fixed to and covering at least a portion of the upper surface of the membrane so as to define a growth region.

5. The method of claim 1, wherein the method further comprises providing a detection reagent, wherein contacting a predefined amount of the inoculum with a growth region of a thin film culture device comprises forming a reconstituted medium comprising the detection reagent.

6. The method of claim 5, wherein the detection reagent comprises an enzyme substrate for a phosphatase enzyme activity.

7. The method of claim 1, wherein incubating the inoculated thin film culture device comprises incubating the reconstituted medium at 25 degrees C. for 72 to 168 hours.

8. The method of claim 1, wherein detecting a presence or an absence of colony of the yeast or mold microorganism comprises detecting the presence or the absence of an osmophilic yeast microorganism or a xerophilic mold microorganism.

9. The method of claim 8, wherein detecting a presence or an absence of colony of the yeast or mold microorganism comprising detecting the presence or the absence of a yeast colony.

10. The method of claim 9, wherein the yeast colony comprises yeast cells of the genus *Zygosaccharomyces*.

11. The method of claim 8, wherein detecting a presence or an absence of colony of the yeast or mold microorganism comprises detecting the presence or the absence of a mold colony.

12. The method of claim 11, wherein the mold colony comprises mold cells of the genus *Fusarium*.

13. The method of claim 1, wherein the aqueous diluent comprises an effective concentration of peptone for facilitating recovery and/or growth of the yeast or mold microorganism.

14. The method of claim 13, wherein the aqueous diluent consists essentially of 0.1% (w/v) peptone and about 1.0% (w/v) to about 10.2% (w/v) glycerol.

15. The method of claim 1, wherein incubating the thin film culture device for a period of time comprises incubating the thin film culture device with a bacteriostatic or bacteriocidal agent included therein.

16. The method of claim 15, wherein the bacteriostatic or bacteriocidal agent comprises chloramphenicol, chlortetracycline, tartaric acid, or a suitable penicillin.

17. The method of claim 1:
wherein the thin film culture device further comprises a cover sheet having a first surface and a second surface, wherein the first surface comprises a second dry gelling agent adhered thereto;
wherein the method further comprises placing the device over the cold water-reconstitutable medium;
wherein placing the device over the cold water-reconstitutable medium comprises contacting a portion of the first surface of the device with the reconstitutable medium.

18. The method of claim 17, wherein the second dry gelling agent comprises guar gum, xanthan gum, or a mixture of guar gum and xanthan gum.

19. The method of claim 9, wherein detecting a presence or an absence of colony of the yeast or mold microorganism comprises detecting a metabolic product of a detection reagent.

20. The method of claim 1, wherein incubating the thin film culture device comprises incubating the reconstituted medium at 25 degrees C. or at 28 degrees C. for 72 to 168 hours.

* * * * *